United States Patent [19]
Dobkowski et al.

[11] Patent Number: 5,961,961
[45] Date of Patent: Oct. 5, 1999

[54] SUNSCREEN COSMETIC COMPOSITION

[75] Inventors: Brian John Dobkowski, Derby; Michael Charles Cheney, Fairfield; Alexander Paul Znaiden, Trumbull; Walter Rose, New Haven, all of Conn.

[73] Assignee: Chesebrough-Pond's USA Co., Greenwich, Conn.

[21] Appl. No.: 09/090,294

[22] Filed: Jun. 4, 1998

[51] Int. Cl.⁶ .................. A61K 7/42; A61K 7/00
[52] U.S. Cl. ............... 424/59; 424/60; 424/400; 424/401
[58] Field of Search ............... 424/59, 60, 400, 424/401

[56] References Cited

U.S. PATENT DOCUMENTS

| | | | |
|---|---|---|---|
| 4,919,934 | 4/1990 | Deckner et al. | 424/401 |
| 4,939,179 | 7/1990 | Cheney et al. | 514/289 |
| 5,188,831 | 2/1993 | Nicoll et al. | 424/401 |
| 5,215,749 | 6/1993 | Nicoll et al. | 424/401 |
| 5,219,558 | 6/1993 | Woodin, Jr. et al. | 424/59 |
| 5,545,399 | 8/1996 | Lee et al. | 424/59 |

*Primary Examiner*—Shelley A. Dodson
*Attorney, Agent, or Firm*—Milton L. Honig

[57] ABSTRACT

A sunscreen cosmetic composition is provided which is a water and emollient oil emulsion containing an inorganic sunscreen agent such as titanium dioxide with a relatively large particle size ranging from about 0.1 to 20 micron and an organic sunscreen agent. High levels of sunscreen activity are achievable without any significant adverse effect on emulsion aesthetics.

10 Claims, No Drawings

SUNSCREEN COSMETIC COMPOSITION

BACKGROUND OF THE INVENTION

1. Field of the Invention

The invention concerns sunscreen compositions, particularly those in emulsion form.

2. The Related Art

Sunscreen compositions are commonly used during outdoor work or leisure for protection of exposed skin against sunburn, cancer and even photo aging. Many effective sunscreen preparations are sold commercially or are described in cosmetic or pharmaceutical literature. In general, sunscreen preparations are formulated as creams, lotions or oils containing as the active agent an ultraviolet radiation absorbing chemical compound. The active agent functions by blocking passage of erythematogenic radiation thereby preventing its penetration into the skin.

The ideal sunscreen formulation should be non-toxic and non-irritating to skin tissue and be capable of convenient application in a uniform continuous film. The product should be sufficiently chemically and physically stable so as to provide an acceptable shelf life upon storage. It is particularly desirable that the preparation should retain its protective effect over a prolonged period after application. Thus, the active agent when present on the skin must be resistant to chemical or photodegradation, to absorption through the skin, and to removal by perspiration, skin oil, or water. For aesthetic reasons, the product should be substantially odorless (or be capable of being scented) and be non-staining to the skin or clothing.

Sunscreen agents in the order of decreasing effectiveness may be categorized as either highly chromophoric monomeric organic compounds, inorganic compounds and minimally chromophoric polymeric organic solids.

U.S. Pat. No. 5,219,558 (Woodin, Jr. et al.) and U.S. Pat. No. 4,919,934 (Deckner et al.) disclose photoprotection compositions wherein the active sunscreen agents are of the chromophoric monomeric organic compound variety. The examples feature the commercially common sunscreens such as octyl methoxycinnamate (Parsol MCX), benzophenone-3(Oxybenzone) and octyl dimethyl PABA.

Chromophoric monomeric organic compounds are subject to certain problems. One of the more important problems is that of skin irritation. Some people are quite sensitive to organic molecules with chromophoric groups. Adverse allergic reactions can result. Therefore, it would be quite desirable to minimize the level of such compounds in sunscreen compositions. Total replacement of chromophoric organic compounds, while desirable, is presently not feasible for high SPF compositions that also require certain types of aesthetics.

Inorganic particulate compounds such as titanium dioxide have been employed as sunscreen agents. In fact, titanium dioxide is quite popular with marketers advertising them as "natural sunscreens". Illustrative of this technology is U.S. Pat. No. 5,215,749 and U.S. Pat. No. 5,188,831, both to Nicoll et al. The problem with inorganic particulate compounds is that high SPF values can only be achieved with high concentrations of these materials. Unfortunately, aesthetics suffer at such high concentrations. Clear formulas become opaque. High loadings also tend to form visible white films on the skin which consumers perceive negatively.

Accordingly, it is an object of the present invention to provide a sunscreen composition in the form of an oil and water emulsion which minimizes the level of potentially irritating organic sunscreens while maximizing the sunscreen protective factor efficiency.

Another object of the present invention is to provide a sunscreen composition in the form of an oil and water emulsion with aesthetic properties substantially undiminished over formulations without any sunscreen.

Still another object of the present invention is to provide a sunscreen composition having much lower human irritancy than formulas of equivalent sun protection factor.

These and other objects of the present invention will more readily become apparent from the description and examples which follow.

SUMMARY OF THE INVENTION

A sunscreen cosmetic composition is provided which includes:

(i) from about 0.01 to about 5% by weight of an oil dispersible inorganic sunscreen particulate having an average particle size of from about 0.1 to about 20 micron;

(ii) from about 0.1 to about 5% by weight of an organic sunscreen agent with a chromophoric group active within the ultraviolet radiation range from 290 to 400 nm;

(iii) from about 0.5 to about 50% by weight of an emollient oil; and (iv) from about 1 to about 90% by weight of water.

DETAILED DESCRIPTION OF THE INVENTION

Now it has been discovered that at lower levels of organic sunscreen agent, a boost in sun protective activity can be achieved by inclusion of large particle size inorganic sunscreen agents. Relatively large particle size, in fact pigment grade, inorganic sunscreen agents such as titanium dioxide and zinc oxide have proved more efficient on a cost basis than micronized sizes. The combination of these sunscreen agents in emulsion cosmetics of the present invention do not significantly interfere with aesthetic properties.

Thus, a first element of the present invention is that of an inorganic sunscreen agent, particularly titanium dioxide and zinc oxide. These agents should be particulates having an average particle size ranging from about 0.1 to about 20 micron (i.e. about 100 nm to about 20,000 nm), preferably from about 0.2 to about 5 micron, more preferably from about 0.25 to about 1.5 micron, optimally from 0.35 to 1.0 micron. Advantageously the agents should be of the oil-dispersible variety exhibiting hydrophobic surface properties. Hydrophobicity may be achieved by applying a hydrophobic coating to the inorganic sunscreen agent particles. Typical coatings include metal soaps, such as aluminum stearate, aluminum laurate or zinc stearate, or coatings with organosilicone compounds. The most preferred agent is titanium dioxide. Amounts of the inorganic sunscreen agent may range from about 0.01 to about 5%, preferably from about 0.05 to about 2%, more preferably from about 0.1 to 0.9%, optimally from about 0.4 to 0.8% by weight.

A second essential element of the present invention is that of an organic sunscreen agent having at least one chromophoric group absorbing within the ultraviolet ranging from 290 to 400 nm. Chromophoric organic sunscreen agents may be divided into the following categories (with specific examples) including: p-Aminobenzoic acid, its salts and its derivatives (ethyl, isobutyl, glyceryl esters;

p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, α-phenyl cinnamonitrile; butyl cinnamoyl pyruvate); Dihydroxycinnamic acid derivatives (umbelliferone, methylumbelliferone, methylacetoumbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxynaphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzone, Sulisobenzone, Dioxybenzone, Benzoresorcinol, 2,2', 4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; Etocrylene; and 4-isopropyl-dibenzoylmethane).

Particularly useful are: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)] aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid and mixtures thereof.

Suitable commercially available organic sunscreen agents are those identified under the following table.

TABLE I

| CTFA NAME | TRADE NAME | SUPPLIER |
|---|---|---|
| Benzophenone-3 | UVINUL M-40 | BASF Chemical Co. |
| Benzophenone-4 | UVINUL MS-40 | BASF Chemical Co. |
| Benzophenone-8 | SPECTRA-SORB UV-24 | American Cyanamid |
| DEA-Methoxycinnamate | BERNEL HYDRO | Bernel Chemical |
| Ethyl dihydroxypropyl-PABA | AMERSCREEN P | Amerchol Corp. |
| Glyceryl PABA | NIPA G.M.P.A. | Nipa Labs. |
| Homosalate | KEMESTER HMS | Humko Chemical |
| Menthyl anthranilate | SUNAROME UVA | Felton Worldwide |
| Octocrylene | UVINUL N-539 | BASF Chemical Co. |
| Octyl dimethyl PABA | AMERSCOL | Amerchol Corp. |
| Octyl methoxycinnamate | PARSOL MCX | Bernel Chemical |
| Octyl salicylate | SUNAROME WMO | Felton Worldwide |
| PABA | PABA | National Starch |
| 2-Phenylbenzimidazole-5-sulphonic acid | EUSOLEX 232 | EM Industries |
| TEA salicylate | SUNAROME W | Felton Worldwide |
| 2-(4-Methylbenzylidene)-camphor | EUSOLEX 6300 | EM Industries |

TABLE I-continued

| CTFA NAME | TRADE NAME | SUPPLIER |
|---|---|---|
| Benzophenone-1 | UVINUL 400 | BASF Chemical Co. |
| Benzophenone-2 | UVINUL D-50 | BASF Chemical Co. |
| Benzophenone-6 | UVINUL D-49 | BASF Chemical Co. |
| Benzophenone-12 | UVINUL 408 | BASF Chemical Co. |
| 4-Isopropyl dibenzoyl methane | EUSOLEX 8020 | EM Industries |
| Butyl methoxy dibenzoyl methane | PARSOL 1789 | Givaudan Corp. |
| Etocrylene | UVINUL N-35 | BASF Chemical Co. |

Amounts of the organic sunscreen agent will range from about 0.1 to about 5%, preferably from about 0.2 to about 2%, more preferably from about 0.6 to about 1.5%, optimally from about 0.8 to about 1.25% by weight.

Sunscreen compositions of the present invention will be emulsions containing an oil and a water phase. Most preferred are oil-in-water emulsions. Water constituting the latter phase will be present in an amount from about 1 to about 90% by weight thereof. Preferably the level of water will range from about 30 to about 90%, optimally between about 80 and about 90% by weight. Water and oil phases may be present in weight ratios of about 200:1 to about 1:10, preferably about 20:1 to about 5:1.

In another aspect of the present invention, it has been found that certain pH ranges improve phase stability and viscosity. More particularly, compositions of the present invention are optimally formulated within a pH range from about 5 to about 7.8, preferably from 5.5 to 7.5, optimally from 5.8 to 6.8.

Further increases in SPF activity can be obtained by incorporation of a $C_2$–$C_2$ amine into compositions of the present invention. Particularly suitable are diethanolamine and triethanolamine (TEA). Best performance results from inclusion of the amine within the oil phase of the emulsion. Suitable levels of amine may range from about 0.05 to about 5%, preferably from about 0.1 to about 2%, more preferably from about 0.3 to about 1%, optimally from about 0.5 to about 0.8% by weight.

Emollient materials will form the oil phase of emulsions according to the present invention. These emollient materials may be selected from hydrocarbons, silicones, fatty alcohols, synthetic or natural esters and combinations thereof. Amounts of the emollient oil will range from about 0.5 to about 50%, preferably from about 1 to about 20%, optimally from about 5 to about 10% by weight.

Hydrocarbons encompass mineral oil, terpenes (such as squalene), isoparaffins and petroleum jelly.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms. Linear volatile silicone materials generally have viscosities less than about 5 centistokes at 25° C. while cyclic materials typically have viscosities of less than about 10 centistokes. Examples of commercially available volatile silicone oils are Dow Corning® 344 and Dow Corning® 345.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Silicone copolyols are useful as emollient and emulsifying materials within the context of the present invention. Particularly preferred is Dow Corning® 3225C fluid, a mixture of cyclomethicone and dimethicone copolyol having viscosity at 25° C. of 600–2000 cps and a specific gravity of about 0.963.

Among the ester emollients are:

(1) Alkenyl or alkyl esters of fatty acids having 10 to 20 carbon atoms. Examples thereof include isoarachidyl neopentanoate, isononyl isononanoate, oleyl myristate, oleyl stearate, octyl stearate and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethyl-ene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate.

(5) Mono-, Di- and Triglyceride esters such as PEG-8 caprylic/capric triglyceride.

(6) Sterols esters, of which cholesterol fatty acid esters are examples thereof.

Most preferred is glycerol monostearate available from Kessco Corporation and Sterols sold under the trademark Generol 122®.

Natural esters which may be employed as emollients include sunflower seed oil, safflower oil, cotton seed oil, rape seed oil, palm kernel oil, palm oil and mixtures thereof.

Fatty alcohols may also serve as emollients. These are typically formed from 10 to 30 carbon atoms and include cetyl, myristyl, palmityl, stearyl, isostearyl, hydroxystearyl, oleyl, linoleyl, behenyl alcohols and mixtures thereof.

Optionally there may be present in the sunscreen emulsion compositions of the present invention a variety of other materials. Examples include fatty acids, humectants, thickeners/viscosifiers, surfactants, preservatives, biologically active materials and other adjunct ingredients. These are described more fully below.

Fatty acids having from 10 to 30 carbon atoms may also be included in the compositions of this invention. Illustrative of this category are pelargonic, lauric, myristic, palmitic, stearic, isostearic, hydroxystearic, oleic, linoleic, ricinoleic, arachidic, behenic and erucic acids. Amounts may range from about 0.1 to about 20%, preferably from about 1 to about 10%, optimally from about 2 to about 5% by weight.

Humectants of the polyhydric alcohol-type can be formulated into the compositions of this invention. The humectant aids in increasing the effectiveness of the emollient, reduces scaling, stimulates removal of built-up scale and improves skin feel. Typical polyhydric alcohols include glycerol (known also as glycerin), polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol. The amount of humectant may range anywhere from about 0.5 to about 30%, preferably between about 1 and about 15% by weight of the composition.

Thickeners/viscosifiers in amounts from about 0.01 to about 5% by weight of the composition may also be included. As known to those skilled in the art, the precise amount of thickeners can vary depending upon the consistency and thickness of the composition which is desired. Exemplary thickeners are xanthan gum, sodium carboxymethyl cellulose, hydroxyalkyl and alkyl celluloses (particularly hydroxypropyl cellulose), and cross-linked acrylic acid polymers such as those sold by B.F. Goodrich under the Carbopol trademark.

Surfactants or emulsifiers can be formulated into cosmetic compositions of the present invention. Total concentration of the surfactant will range from about 0.1 to about 40%, preferably from about 1 to about 20%, optimally from about 1 to about 5% by weight of the total composition. The surfactant may be selected from the group consisting of anionic, nonionic, cationic and amphoteric actives. Particularly preferred nonionic surfactants are those with a $C_{10}14$ $C_{20}$ fatty alcohol or acid hydrophobe condensed with from about 2 to about 100 moles of ethylene oxide or propylene oxide per mole of hydrophobe; the $C_2$–$C_{10}$ alkyl phenols condensed with from 2 to 20 moles of alkylene oxide; mono- and di-fatty acid esters of ethylene glycol; fatty acid monoglyceride; sorbitan, mono- and di-$C_8$–$C_{20}$ fatty acids; and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates and combinations thereof.

Advantageously compositions of the present invention may exhibit higher SPF activity when based upon purely nonionic surfactant systems (with anionic surfactants being absent). Most preferred are nonionic surfactants of HLB values higher than about 11.5, preferably higher than about 12.5 and optimally between about 13 and 20.

Compositions of the present invention may also contain $C_1$–$C_{20}$ α-hydroxycarboxylic acids and salts thereof. The salts are preferably alkalimetal, ammonium and $C_1$–$C_{12}$ alkanolammonium salts. Illustrative acids are glycolic acid, lactic acid and 2-hydroxycaprylic acid. Most preferred is a combination of glycolic and 2-hydroxycaprylic acids and their ammonium salts. Levels of these materials may range from about 0.01 to about 15%, preferably from about 0.1 to about 9%, optimally between about 0.5 and about 7% by weight of the cosmetic composition.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are disodium EDTA, phenoxyethanol, methyl paraben, propyl paraben, imidazolidinyl urea (commercially available as Germall 1157), sodium dehydroacetate and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition.

Minor adjunct ingredients may also be present in the cosmetic compositions. These ingredients include vitamins (such as Vitamin $B_6$, Vitamin C, ascorbyl palmitate, Vitamin A palmitate, Vitamin E acetate, biotin, niacin and DL-panthenol), amino acids (such as glycine and serine), ceramides (such as Ceramide 1, Ceramide 3 and Ceramide 6), bio-hyaluronic acid (with oligosaccharides, available as Actiglide J® from Active Organics US) and sodium PCA.

Colorants, fragrances, opacifiers and abrasives may also be included in compositions of the present invention. Each of these substances may range from about 0.05 to about 5%, preferably between about 0.1 and about 3% by weight.

Except in the operating and comparative examples, or where otherwise explicitly indicated, all numbers in this description indicating amounts of material are to be understood as modified by the word "about".

The following Examples will more fully illustrate the embodiments of this invention. All parts, percentages and proportions referred to herein and in the appended claims are by weight unless otherwise indicated.

EXAMPLES 1–8

The following examples are illustrative of formulations according to the present invention.

TABLE I

| COM-PONENTS | EXAMPLE | | | | | | | |
|---|---|---|---|---|---|---|---|---|
| | 1 | 2 | 3 | 4 | 5 | 6 | 7 | 8 |
| Oil Phase | | | | | | | | |
| Stearic Acid | 2.50 | 2.50 | 2.50 | 2.50 | 2.50 | 2.50 | 2.50 | 2.50 |
| Glycerol Monostearate | 2.20 | 2.20 | 2.20 | 2.20 | 2.20 | 2.20 | 2.20 | 2.20 |
| Cetyl Alcohol | 0.40 | 0.40 | 0.40 | 0.40 | 0.40 | 0.40 | 0.40 | 0.40 |
| Sunflower Seed Oil | 2.00 | 2.00 | 2.00 | 2.00 | 2.00 | 2.00 | 2.00 | 2.00 |
| Vitamin E Acetate | 0.01 | 0.01 | 0.01 | 0.01 | 0.01 | 0.01 | 0.01 | 0.01 |
| Parsol MCX ® | 2.00 | 1.50 | 1.25 | 1.00 | 0.80 | 0.60 | 0.50 | 1.00 |
| Triethanolamine | 0.80 | 0.80 | 0.80 | 0.80 | 0.80 | 0.80 | 0.80 | 0.80 |
| Lecithin | 0.04 | 0.04 | 0.04 | 0.04 | 0.04 | 0.04 | 0.04 | 0.04 |
| Water Phase | | | | | | | | |
| Glycerin | 0.50 | 0.50 | 0.50 | 0.50 | 0.50 | 0.50 | 0.50 | 0.50 |
| Carbopol 934 ® (2% active) | 3.00 | 3.00 | 3.00 | 3.00 | 3.00 | 3.00 | 3.00 | 3.00 |
| Gel White GP ® | 0.20 | 0.20 | 0.20 | 0.20 | 0.20 | 0.20 | 0.20 | 0.20 |
| Glydant Plus ® | 0.09 | 0.09 | 0.09 | 0.09 | 0.09 | 0.09 | 0.09 | 0.09 |
| Colorant | 0.39 | 0.39 | 0.39 | 0.39 | 0.39 | 0.39 | 0.39 | 0.39 |
| Fragrance | 0.25 | 0.25 | 0.25 | 0.25 | 0.25 | 0.25 | 0.25 | 0.25 |
| Titanium Dioxide (300 nm) | 0.01 | 0.05 | 0.10 | 0.20 | 0.30 | 0.60 | 0.80 | 1.00 |
| Disodium EDTA | 0.05 | 0.05 | 0.05 | 0.05 | 0.05 | 0.05 | 0.05 | 0.05 |
| Water | qs | qs | qs | qs | qs | qs | qs | qs |

EXAMPLE 9

A series of comparative experiments were performed to demonstrate the synergistic effect between a typical organic sunscreen such as octyl methoxycinnamate (Parsol MCX®) and oil dispersible pigment grade (0.28 micron) titanium dioxide.

TABLE II

| DESCRIPTION | FORMULATION (WEIGHT %) | | | |
|---|---|---|---|---|
| Oil Phase | A | B | C | D |
| Stearic Acid | 2.54 | 2.54 | 2.54 | 2.54 |
| Glycerol Monostearate/Stearamide | 1.50 | 1.50 | 1.50 | 1.50 |
| Glycerol Monostearate | 0.70 | 0.70 | 0.70 | 0.70 |
| Cetyl Alcohol | 0.40 | 0.40 | 0.40 | 0.40 |
| Soya Sterol | 0.08 | 0.08 | 0.08 | 0.08 |
| Vitamin E Acetate | 0.01 | 0.01 | 0.01 | 0.01 |
| Lecithin | 0.04 | 0.04 | 0.04 | 0.04 |
| Sunflower Seed Oil | 1.25 | 1.25 | 1.25 | 1.25 |
| Parsol MCX ® | | 1.25 | | 1.25 |
| Titanium Dioxide (300 nm) (oil dispersible) | | | 0.80 | 0.80 |
| Silicone Oil | 0.20 | 0.20 | 0.20 | 0.20 |
| Water Phase | | | | |
| Disodium EDTA | 0.05 | 0.05 | 0.05 | 0.05 |
| Veegum ® | 0.20 | 0.20 | 0.20 | 0.20 |
| Glycerin | 5.50 | 5.50 | 5.50 | 5.50 |
| Carbopol 934 (2% aqueous sol) | 3.00 | 3.00 | 3.00 | 3.00 |
| Triethanolamine | 0.80 | 0.80 | 0.80 | 0.80 |
| Glydant Plus ® | 0.09 | 0.09 | 0.09 | 0.09 |
| Colorant | 0.39 | 0.39 | 0.39 | 0.39 |
| Fragrance | 0.15 | 0.15 | 0.15 | 0.15 |
| Vitamin A Palmitate | 0.001 | 0.001 | 0.001 | 0.001 |
| Water | balance | balance | balance | balance |

TABLE III

| | FORMULATION (WEIGHT %) | | | |
|---|---|---|---|---|
| SUNSCREEN ACTIVES | A | B | C | D |
| Octyl Methoxycinnamate | | 1.25 | | 1.25 |
| Titanium Dioxide (Oil Dispersible) | | | 0.8 | 0.8 |
| ACTIVITY | | | | |
| In Vitro SPF Results | 1 | 1.86 | 1.3 | 2.9 |
| SPF Without Base | | 0.86 | 0.3 | 1.9 |

The results in Table III reveal that the combination of Parsol MCX® and pigment grade titanium dioxide provide a synergistic effect at relatively low concentrations. This effect is 0.74 extra units of SPF or a 63% boost over the sum of each active alone.

EXAMPLE 10

Experiments presented under this Example are directed to demonstrate that lower concentrations of organic sunscreen provide a higher SPF on a per weight basis. Other than the concentration of actives, the formulations were identical to those reported in Table II of Example 9.

TABLE IV

| SUNSCREEN ACTIVES | FORMULATION (WEIGHT %) | | | |
|---|---|---|---|---|
|  | A | B | C | D |
| Octyl Methoxycinnamate | 0.6 | 1.25 | 2 | 4 |
| Titanium Dioxide (Oil Dispersible) | 0.8 | 0.8 | 0.8 | 0.8 |
| ACTIVITY |  |  |  |  |
| In Vitro SPF Results | 2.26 | 2.9 | 4.26 | 7.14 |
| Parsol MCX/SPF Efficiency Ratio | 3.7 | 2.32 | 2.13 | 1.79 |

Efficiency ratios listed in Table IV show a decrease as the concentration of octyl methoxycinnamate increases from 0.6 to 4%. Best efficiency is achieved below 2% organic sunscreen.

EXAMPLE 11

Further experiments were conducted to evaluate the effect of including an amine in the oil or aqueous phase. Other than the actives, the formulations are those reported in Example 9 (Table II).

TABLE V

| ACTIVE | FORMULATIONS (WEIGHT %) | | | | |
|---|---|---|---|---|---|
|  | A | B | C | D | E |
| Octyl Methoxycinnamate | 1.25 | 1.25 | 1.25 | 1.25 |  |
| Titanium Dioxide (Oil Dispersible) | 0.8 | 0.8 | 0.8 | 0.8 | 0.8 |
| TEA (Oil Phase) | 0 | 0.1 | 0.8 | 1.4 | 2.8 |
| Stearic Acid | 2.54 | 2.54 | 2.54 | 2.54 | 2.54 |
| STABILITY |  |  |  |  |  |
| At 60° C. Appearance | phase separation | slight phase separation | ok | ok | slight phase separation |
| At 60° C. Viscosity (cps) | very thin 300 cps | good viscosity 10,700 cps | good viscosity 19,300 cps | sl thin 11,000 cps | thin 3,650 cps |
| Freeze/Thaw Cycle Appearance | phase separation | slight phase separation | ok | ok | ok |
| Freeze/Thaw Viscosity (cps) | very thin 250 cps | thin 7,300 cps | good viscosity 11,900 cps | thin 9,200 cps | sl thin 7,600 cps |
| At 25° C. Appearance | phase separation | translucent | good creamy | good creamy | good creamy |
| At 25° C. Viscosity (cps) | very thin 200 cps | thin 6,850 cps | good viscosity 10,700 cps | thin 7,750 cps | thin 6,300 cps |
| Overall Stability | unaccept. phase separation | unaccept. sl phase separation | accept. no phase separation | unaccept. too thin | unaccept. too thin |

Table V reveals that at relatively high or low levels of base (triethanolamine), phase stability is poor. The optimum range lies somewhere between about 0.3 and about 1%.

EXAMPLE 12

Experiments detailed under this Example evaluate the effect of surfactant type on the SPF activity. Other than the actives and surfactants, the formulations were identical to those reported under Example 9 (Table II).

TABLE VI

| ACTIVE | FORMULATION (WEIGHT %) | | | | |
|---|---|---|---|---|---|
|  | A | B | C | D | E |
| Octyl Methoxycinnamate | 0.6 | 0.6 | 0.6 | 0.6 | 0.6 |
| Titanium Dioxide (Oil Dispersible) | 0.8 | 0.8 | 0.8 | 0.8 | 0.8 |
| TEA (Water Phase) | 0.8 |  |  |  | 1.8 |
| Anionic Surfactant (TEA Stearate) | 3.34 |  |  |  |  |
| Nonionic (PEG-100 Stearate) |  |  | 0.8 | 3.34 |  |
| Cationic (Distearyl Dimonium Chloride) |  | 3.34 |  |  |  |
| Total Surfactant Content | 3.34 | 3.34 | 3.34 | 3.34 | 6.68 |
| ACTIVITY |  |  |  |  |  |
| In Vitro SPF Results | 1.9 | 2.3 | 3.5 | 4.3 | 2 |

The results in Table VI show that a nonionic surfactant system provides a higher SPF than either an anionic or cationic surfactant system. A higher HLB also improves the sunscreen activity.

EXAMPLE 13

Experiments under this Example demonstrate the effect of having an amine present in either the water or oil phase. Other than the actives, the formulations were identical to those reported under Example 9 (Table II).

TABLE VII

| ACTIVE | FORMULATION (WEIGHT %) | | | |
|---|---|---|---|---|
|  | A | B | C | D |
| Octyl Methoxycinnamate | 0.00 | 0.00 | 1.25 | 1.25 |
| Titanium Dioxide (Oil Dispersible) | 0.00 | 0.00 | 0.80 | 0.80 |
| TEA (Water Phase) | 0.80 |  | 0.80 |  |
| TEA (Oil Phase) |  | 0.80 |  | 0.80 |
| ACTIVITY |  |  |  |  |
| In Vitro SPF Results | 1 | 1 | 2.9 | 3.28 |

The results reported in Table VII reveal that TEA in the oil phase provides a greater boost to SPF than when in the water phase. Of course, the presence of the amine in either water or oil phase improves sunscreen activity.

EXAMPLE 14

Experiments outlined in this Example demonstrate the desirability of oil rather than water dispersible, large particle size titanium dioxide. Other than the titanium dioxide, the compositions of the formulations were identical to those reported under Example 9 (Table II). The amount of Parsol MCX® was held at 1.25%.

TABLE VIII

| ACTIVE | FORMULATION (WEIGHT %) | |
| --- | --- | --- |
| | A | B |
| Titanium Dioxide (Oil Dispersible) | 0.8 | |
| Titanium Dioxide (Water Dispersible) | | 0.8 |
| Appearance | smooth | grainy/lumpy |

Table VIII demonstrates the preference for oil dispersible type titanium dioxide; a smooth and lump free product is obtained. Water dispersible variety is unacceptable.

EXAMPLE 15

Experiments recorded under this Example demonstrate the effect of pH on the SPF activity. Other than the actives and triethanolamine, the formulations were identical to those reported under Example 9 (Table II).

TABLE IX

| ACTIVE | FORMULATION (WEIGHT %) | | | | | |
| --- | --- | --- | --- | --- | --- | --- |
| | A | B | C | D | E | F |
| Octyl Methoxycinnamate | 1.25 | 1.25 | 1.25 | 1.25 | 1.25 | 1.25 |
| Titanium Dioxide (Oil Dispersible) | 0.8 | 0.8 | 0.8 | 0.8 | 0.8 | 0.8 |
| TEA % (Oil Phase) | 0 | 0.1 | 0.8 | 1.4 | 0 | 0 |
| TEA % (Water Phase) | 0 | 0 | 0 | 0 | 0.1 | 0.8 |
| Stearic Acid | 2.54 | 2.54 | 2.54 | 2.54 | 2.54 | 2.54 |
| pH | 5 | 6 | 7 | 8 | 6 | 7 |
| Activity | | | | | | |
| In Vitro SPF Results | 4.2 | 4.4 | 2.86 | 2.82 | 4.1 | 2.9 |

Table IX demonstrates that there is an approximately 50% increase in SPF with pH lower than 7. The pH effect is present whether or not TEA is formulated into the oil or water phase. The operative range of pH appears to be between about 5 and about 7.5, but best between 5.5 and 7.0.

EXAMPLE 16

A further set of experiments were conducted to evaluate the effect of cations on SPF activity. Other than the actives, TEA and other counterions, the formulations were identical to those reported under Example 9 (Table II).

TABLE X

| ACTIVE | FORMULATION (WEIGHT %) | | | | |
| --- | --- | --- | --- | --- | --- |
| | A | B | C | D | E |
| Octyl Methyoxycinnamate | 1.25 | 1.25 | 1.25 | 1.25 | 1.25 |
| Titanium Dioxide (Oil Dispersible) | 0.8 | 0.8 | 0.8 | 0.8 | 0.8 |
| Active | | | | | |
| TEA (Water Phase) | pH 7.0 | | | | |
| Sodium Hydroxide | | pH 7.0 | | | |
| Potassium Hydroxide | | | pH 7.0 | | |
| Ammonium Hydroxide | | | | pH 7.0 | |
| Calcium Hydroxide | | | | | pH 7.0 |
| Stearic Acid | 2.54 | 2.54 | 2.54 | 2.54 | 2.54 |
| Activity | | | | | |
| In Vitro SPF Results | 2.9 | 5.9 | 4.9 | 3.6 | 5.56 |
| % Boost From TEA | | 96 | 71 | 24 | 91 |

The results shown in Table X indicate that there is a significant boost in SPF when utilizing an inorganic cation to neutralize stearic acid. Sodium and calcium are the most effective. The study was conducted at pH 7.0 (0.8% TEA equivalent).

The foregoing description and Examples illustrate selected embodiments on the present invention. In light thereof, various modifications will be suggested to one skilled in the art, all of which are within the spirit and purview of this invention.

The term "comprising" is meant not to be limiting to any subsequently stated elements but rather to encompass non-specified elements of major or minor functional importance. In other words the listed steps, elements or options need not be exhaustive.

What is claimed is:

1. A sunscreen cosmetic composition comprising:
   (i) from about 0.01 to about 5% by weight of an oil dispersible inorganic sunscreen particulate having an average particle size of from about 0.1 to about 20 micron;
   (ii) from about 0.1 to about 5% by weight of an organic sunscreen agent with a chromophoric group active within the ultraviolet radiation range from 290 to 400 nm;
   (iii) from about 0.5 to about 50% by weight of an emollient oil; and
   (iv) from about 1 to about 90% by weight of water.

2. The composition according to claim 1 wherein the organic sunscreen agent is selected from the group consisting of benzophenone-3, benzophenone-4, benzophenone-6, benzophenone-8, benzophenone-12, butyl methoxy dibenzoyl methane, PABA, octyl dimethyl PABA, octyl methoxycinnamate and combinations thereof.

3. The composition according to claim 2 wherein the organic sunscreen agent is octyl methoxycinnamate.

4. The composition according to claim 1 wherein the inorganic sunscreen agent is selected from the group consisting of titanium dioxide and zinc oxide.

5. The composition according to claim 1 wherein the average particle size ranges from 0.25 to 1.5 micron.

6. The composition according to claim 1 wherein the inorganic sunscreen agent is present in an amount from about 0.1 to 0.9% by weight.

7. The composition according to claim 1 having a pH ranging from about 5 to about 7.5.

8. The composition according to claim 1 further comprising a $C_2$–$C_{20}$ amine in an amount from about 0.1 to about 2% by weight.

9. The composition according to claim 8 wherein the amine is triethanolamine.

10. The composition according to claim 8 wherein the amine is dispersed in an oil phase of the composition.

* * * * *